United States Patent

Boltze et al.

[11] 3,966,956
[45] June 29, 1976

[54] [1-(p-CHLOROBENZOYL)-5-METHOXY-2-METHYL-3-INDOLE]ACETOXYACETIC ACID AND SALTS IN TREATING INFLAMMATION

[75] Inventors: Karl-Heinz Boltze, Bensberg-Kippekausen; Otfried Brendler, Cologne; Hans-Dieter Dell, Bergisch-Gladbach; Haireddin Jacobi, Leichlingen, all of Germany

[73] Assignee: Troponwerke Dinklage & Company, Cologne, Germany

[22] Filed: Apr. 9, 1975

[21] Appl. No.: 566,452

Related U.S. Application Data

[63] Division of Ser. No. 374,615, June 28, 1973, Pat. No. 3,910,952.

[30] Foreign Application Priority Data

July 14, 1972 Germany............................ 2234651

[52] U.S. Cl. ................................................ 424/274
[51] Int. Cl.² .......................................... A61K 31/40
[58] Field of Search ...................................... 424/274

*Primary Examiner*—Stanley J. Friedman
*Attorney, Agent, or Firm*—Burgess, Dinklage & Sprung

[57] ABSTRACT

[1-(p-chlorobenzoyl)-5-methoxy-2-methyl-3-indole]-acetoxyacetic acid of the formula

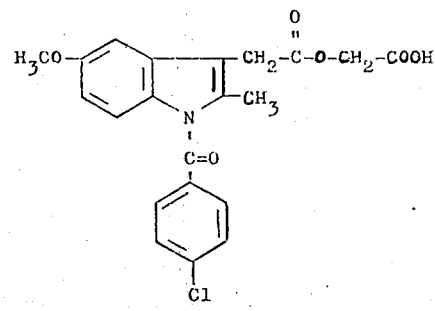

possesses outstanding antiphlogistic activity without the side effects of certain conventional antiphlogistic pharmaceuticals.

9 Claims, No Drawings

[1-(P-CHLOROBENZOYL)-5-METHOXY-2-METHYL-3-INDOLE]ACETOXYACETIC ACID AND SALTS IN TREATING INFLAMMATION

This is a continuation of application Ser. No. 374,615, filed June 28, 1973, now U.S. Pat. No. 3,910,952.

The present invention relates to a novel [1-(p-chlorobenzoyl)-5-methoxy-2-methyl-3-indole]-acetoxyacetic acid and its salts formed with pharmacologically acceptable bases. The invention further relates to processes for the production of the new compound and its use in medicines, more particularly in medicines with an antiphlogistic effect.

The invention therefore provides [1-(p-chlorobenzoyl)-5-methoxy-2-methyl-3-indole]-acetoxyacetic acid, which has the formula

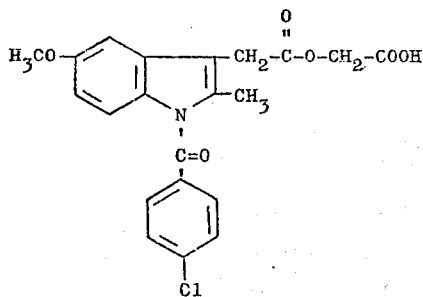

Antiphlogistic properties are claimed in literature for other compounds with this basic polynuclear chemical structure. The best known member of this class is 1-(p-chlorobenzoyl)-5-methoxy-2-methyl-3-indole acetic acid (hereinafter referred to as II), which is used in human medicine under the name of "Indomethacin". The compound, however, has a number of undesirable side effects.

Thus, J. Solinca (Arzneimittelforschung 21, No. 11a (1971) page 1834) has very frequently observed, as relatively slight side effects, neurosensitive disturbances such as headaches, vertigos and concentration difficulties, digestive complaints with loss of appetite, sickness, stomach pains, diarrhoea and, finally, some serious cases of intestinal bleeding, stomach ulcers and, occasionally, neurological deficiency symptoms. G. Morandi and U. Serni (Arzneimittelforschung 21, 11a (1971), page 1834) found that, with practically 10% of patients, therapy with II had to be discontinued because of the side effects.

An object of this invention was therefore to synthesise a compound of a similar class which was less toxic than II, while having equally good or better antiphlogistic activity so that fewer side effects were to be expected.

It was found that the new compound I is characterised by a strong antiphlogistic effect. On the kaolin oedema of the paw of a rat, an $ED_{50}$ of 0.50

$$\begin{bmatrix} 0.67 \\ 0.37 \end{bmatrix} \text{ mg/kg}$$

was established with a single oral application. The $ED_{50}$ is defined as the dose which reduces the oedemas of a group of animals treated with I by half as compared with a control group (the values in parentheses indicate the range of confidence for a probability of error of P = 5%).

By contrast, using the compound II, an $ED_{50}$ of 1.04

$$\begin{bmatrix} 1.40 \\ 0.83 \end{bmatrix} \text{ mg/kg}$$

was found so that, in this experiment, I is about twice as effective as II.

The difference between the two $ED_{50}$ values is statistically significant.

Furthermore, with two other forms of inflammation, the inflammations produced with formalin and carrageenin on the paw of a rat, the oedema-inhibiting efficiency of I is stronger than that of II. Thus, a dose of 1.5 mg/kg of I, applied once orally, inhibits formalin oedema by 25% and carrageenin oedema by 62%, while the inhibiting action of 1.6 mg/kg of II, applied in the same way, is 13.8% with the formalin oedema and 42% with the carrageenin oedema. These differences are also statistically significant.

I likewise has a strong inflammation-inhibiting efficiency on arthritis produced in the rat with Freud's adjuvants (see, for example, E.M. Glenn and J. Grey, Am. J. Vet. Res. 26 (1965), pages 1180–93); this was the case both in respect of the primary inflammation symptoms formed at the point of injection and also as regards the generalised inflammation symptoms occurring after about 14 days. The antiphlogistic effect of a daily dose of 3.5 mg/kg of I, administered orally, is decidedly stronger than that of the equimolar daily dose of 3 mg/kg of II.

It was also possible to confirm the superiority of I over II in Mizushima's Test in which potent antiphlogistics are known to inhibit protein hazing directly proportional to their antiphlogistic potency (cf. Arch. int. Pharmacodyn. 149 (1964), 1, and 157 (1965), 115).

A $DE_{50}$ of 0.07 mg/ml was measured for the sodium salt of I, in other words the level of protein hazing was inhibited by 50% at this concentration. Chemical analysis carried out at the same time showed that this protective effect is attributable solely to the intact compound I.

By contrast, a concentration of 0.13 mg/ml was required to obtain the same effect with II.

Another characteristic test for determining the activity of non-steroid antiphlogistic substances is the method described by D. A. Gerber, N. Cohen and R. Giustra (cf. Biochem. Pharmacol. 16 (1967) 115) of influencing the physical-chemical behaviour of native protein, for example influencing the reaction velocity of the sulphydryl groups present in the serum with 2,2'-dinitro-5,5-dithiobenzoic acid. In a concentration range of 0.5 to 3 mMol/liter of compound I, the increase in reaction velocity amounted to 105–335% as against an increase of 39–272% with corresponding concentration of II. Since, according to Gerber et al, (loc. cit.), the percentage increase in reaction velocity is directly proportional to antiphlogistic activity, a greater activity of I by comparison with II can also be derived from this in vivo test; this applies above all in the lower concentration ranges (105:39) which come closest to the therapeutically attainable concentrations. In this case, too, the intact compound I can be shown to be the only active component.

Another interesting criterion for the activity of a pharmacon is protein binding. It is known that, in the serum, pharmacons are partly bound to protein and it is only those fractions that are not bound to protein which are responsible for the onset of biological activity. Comparison of the protein binding of I and II by the ultracentrifuging method (cf. inter alia II. Buttner & F. Portwich, Arzneimittelforschung 11 (1961), 1133, or W. Schotan, Arzneimittelforsch. 15 (1965), 1433), showed a higher concentration of non-protein-bound I in the serum for I than for II. Where human albumin is used, the differences amount to about 60%, in other words, for the same protein concentration and an equivalent substance concentration, the values for non-protein-bound I are about 60% higher than those of II. The values found for II are consistent with those described in the literature (cf. E. Hvidberg et al, Eur. J. clin. Pharmacol. 4 (1972), 119). Accordingly, I can be expected to show greater activity in this test as well, i.e. a smaller dosage of I is required which can again be of advantage in toxicological terms.

As shown by tests on dogs, I is well resorbed after oral administration and can be detected as an unchanged molecule for several hours in the organism.

The toxicity data ($LD_{50}$) of both compounds are as follows:

As regards I, after single oral administration of 55.5 mg/kg to the mouse and 38.9 mg/kg to the rat (using the sodium salt of I). The corresponding data for II are 18.4 and 24.5 mg/kg, respectively. Consequently, I had a decidedly stronger antiphlogistic efficiency than II while being of lower toxicity, so that a broader therapeutic range is to be expected with use for medicinal purposes.

The invention also relates to the production of the new compound I. It can be produced by splitting its benzyl ester by hydrogenation as known per se. The reaction is preferably carried out in the presence of catalysts with a hydrogenating effect. Particularly suitable catalysts are metal catalysts from Group Eight of the Periodic System, for example finely divided palladium. The hydrogenating splitting reaction can be carried out in an inert solvent. Hydrogenation is carried out for example at room temperature or only slightly elevated temperatures.

The benzyl ester of I can be obtained in different ways. It can be prepared for example, by A. condensing 4-methoxyphenylhydrazine or its salts with benzyl levulinoyloxyacetate according to Fischer to form (5-methoxy-2-methyl-3-indoleacetoxy)-benzyl acetate, subsequently acylating the alkali salt thereof with p-chlorobenzoyl chloride to form [1-(p-chlorobenzoyl)-5-methoxy-2-methyl-3-indoleacetoxy]-benzyl acetate and then catalytically dehydrogenating the benzyl group (see reaction scheme A), B. by condensing N⁽¹⁾-4-methoxyphenyl-4-chlorobenzhydrazide with benzyl levulinoyloxyacetate according to Fischer to form [1-(p-chlorobenzoyl-5-methoxy-2-methyl-3-indoleacetoxy]-benzyl acetate and thereafter catalytically dehydrogenating the benzyl group (see reaction scheme B), C. condensing the alkali salt of 1-(p-chlorobenzoyl)-5-methoxy-2-methyl-3-indoleacetic acid with benzyl chloroacetate or benzyl bromoacetate and thereafter catalytically dehydrogenating the benzyl group (see reaction scheme C), D. reacting benzyl levulinoyloxyacetate with 4-methoxy phenylhydrazine to form the corresponding hydrazone, acylating this latter with p-chlorobenzoyl chloride, thereafter subjecting it to an indole condensation according to Fischer and debenzylating the [1-(p-chlorobenzoyl)-5-methoxy-2-methyl-3-indoleacetoxy]-benzyl acetate by catalytic hydrogenation (see reaction scheme D) or E. acylating (5-methoxy-2-methyl-3-indoleacetoxy)-benzyl acetate with the mixed anhydride of p-chlorobenzoic acid and a monoalkyl carbonic ester in the presence of bases and thereafter splitting off the benzyl group by catalytic hydrogenation (see reaction scheme E).

The free acid I can be converted into its salts in a manner known per se. Pharmacologically acceptable and conventional inorganic and organic bases can be considered for this purpose. Salts which are soluble in water or aqueous-alcoholic solution for example alkali salts are generally preferred. For pharmacological use of the new compound I, the sodium salt in particular shows an interesting property. If the sodium salt of the known compound II is dissolved in water or water/alcohol, then there is, almost immediately, a clouding of the solution and the compound II begins to decompose. On the other hand, if the sodium salt of the compound I according to the invention is dissolved in such aqueous or aqueous-alcoholic liquids, then the solution remains clear for a considerable period of time. Freshly prepared solutions of the sodium salt can consequently be injected and are, in particular, also suitable for intravenous injection.

The benzyl levulinoyloxyacetate and 4-methoxyphenylhydrazine used as starting compounds for the process according to A are known from the literature. The said hydrazine can be used as a free base; because of its comparatively low stability, however, it is advantageous to use its salts with inorganic acids, more particularly the hydrochloride. Derivatives of 4-methoxyphenylhydrazine can also be used, for example, the sodium salt of 4-methoxy-phenylhydrazine-β-sulphonic acid. Alcohols, such as methanol, ethanol, propanol and isopropanol, can be used as diluents; benzyl alcohol is particularly preferred for this purpose, since with this the danger of re-esterification is avoided.

All base-combining agents can be used as condensation agents. These include mineral acids, such as hydrochloric acid, concentrated sulphuric acid, phosphoric acid or also zinc chloride, as well as lower aliphatic acids, such as formic acid, acetic acid and propionic acid. It is particularly desirable to use glacial acetic acid, which can at the same time also be used as solvent, or a mixture of glacial acetic acid and hydrogen chloride.

The reaction temperatures can be varied within a relatively wide range. Generally, a temperature between room temperature and 100°C is used. In the lower temperature range, the reaction takes place more slowly, but yields very pure condensation products; in the upper temperature range, the reaction takes place more quickly, but the condensation products are obtained in a less pure form.

The subsequent acylation of the (5-methoxy-2-methyl-3-indoleacetoxy)-benzyl acetate obtained by the foregoing condensation with p-chlorobenzoyl chloride is preferably effected by way of its sodium salt. The sodium salt is preferably prepared by using sodium hydride or phenyl sodium. As diluent or suspension medium, dimethylformamide and, in the case of sodium hydride, also suspensions in mineral oil, have proved suitable. The reaction temperatures lie in the range from −10° to +10°C, more particularly 0 to 5°C. The use of sodium hydride in dimethylformamide is particularly suitable, since the subsequent acylation with p-chlorobenzoyl chloride or bromide can be carried out in the same diluent and at the same temperature in a single vessel process.

When carrying out the acylation, 1 to 3 mols of the acid halide, more particularly 1.5 to 2 mols, are used in excess to 1 mol of the indole sodium salt.

The subsequent splitting of the benzyl group from the [1-(p-chlorobenzoyl)-5-methoxy-2-methyl-3-indoleacetoxy]-benzyl acetate prepared by the foregoing methods is preferably effected by hydrogenation on a palladium carbon catalyst. As diluent, all inert organic solvents may be considered. These advantageously include higher hydrocarbons, such as benzene, toluene, xylene, ethers such as higher aliphatic ethers, cycloaliphatic ethers such as dioxan, tetrahydrofuran, as well as aliphatic lower alcohols such as ethanol and isopropanol. Dimethylformamide and ethyl acetate are particularly preferred. Reaction temperatures for the hydrogenation can be varied between 20° and 60°C and preferred temperatures are about 20°C.

The preparation of the compound I according to the invention, using the process B, can be carried out under similar conditions to those mentioned under the process A. For the Fischer-indole condensation, instead of 4-methoxyphenyl hydrazine or its salts, $N^{(1)}$-(p-methoxyphenyl)-p-chlorobenzhydrazide or its salts with organic acids, are used here, more particularly the hydrochloride, which substance is also being known from the literature.

If the compound I according to the invention is to be produced by the process C, then the 1-(p-chlorobenzoyl)-5-methoxy-2-methyl-3-indole-acetic acid used as the starting material is preferably first converted to the sodium or potassium salt. In the case of the sodium salt, the acid is dissolved in a lower aliphatic alcohol, such as methyl, ethyl or isopropyl alcohol, and a solution of an equivalent quantity of potassium hydroxide in alcohol is added to the said solution. After concentration of the solution by evaporation under vacuum at temperatures which should not exceed 20°C, the residue is gently heated for several hours with a solution of equimolar quantities of phenyl-bromoacetate in dimethylformamide, preferably at 50°C. A particularly convenient and therefore preferred method of preparation of I consists in dissolving 1-(p-chlorobenzoyl)-5-methoxy-2-methyl-3-indoleacetic acid in dimethylformamide, stirring with the equivalent quantity of powdered sodium carbonate and thereafter heating with an equivalent quantity of benzylbromoacetate or benzylchloracetate. The subsequent hydrogenation takes place as described under process A.

Another method of preparing the compound I according to the invention is the acylation of (5-methoxy-2-methyl-3-indoleacetoxy)-benzyl acetate and subsequently splitting off the benzyl group. The mixed anhydride of p-chlorobenzoic acid with a monoalkyl ester of carbon dioxide is preferably used as acylation agent for this purpose. The reaction takes place by simply mixing the reactants and slowly heating them to 200°C until the evolution of carbon dioxide, starting at about 80°C, has ended. It is advantageous to use an excess of anhydride, preferably in the ratio of 1:2 to 1:3. The reaction takes place in the presence of a catalytic quantity of an organic base. As the organic base it is possible, inter alia, to use quinoline and pyridine and, more particularly triethylamine. The subsequent hydrogenation of the [1-(p-chlorobenzoyl)-5-methoxy-2-methyl-3-indoleacetoxy]-benzyl acetate which is formed takes place as described under A.

The strong antiphlogistic effect of the new compound I, which is far superior to that known from the prior art, with its simultaneously lower toxicity, is absolutely unparalleled within the class of substances. Many derivatives of the polynuclear basic structure which is shown herein and closely related in structure to the compounds I and II were tested for their antiphlogistic efficiency. It established in all cases that neither the effect of the known compound II or the greatly improved effect of the compound I according to the invention, could be obtained. The following derivatives of closely related structure were investigated:

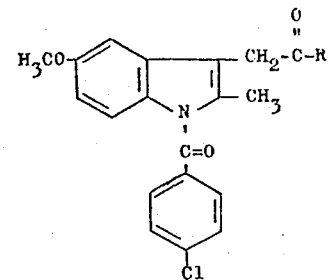

in which

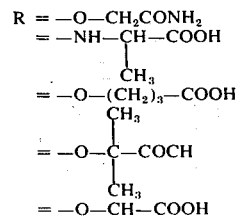

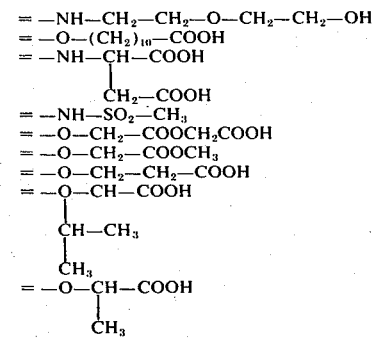

The antiphlogistic effect of all these compounds is far below that of the compound I according to the invention and also far below that of II. With the components showing the highest activity, it was possible to achieve 1/10 of the efficiency of I and, in many cases, the best result obtained was 1/100 of the efficiency of I.

The new active compounds can be transformed in known manner into the usual formulations, such as tablets, capsules, dragees, pills, granules, suppositories, ointments, pastes, creams, lotions, powders, solutions, syrups and emulsions. The formulations can be produced with the use of auxiliary substances. Such auxiliary substances include fillers, disintegrating agents, binders, lubricants and anti-agglutinants. Fillers are inter alia maize starch, lactose, milk sugar, sodium chloride and starch.

The disintegrating agents include maize starch, alginic acid and its alginates.

Gelatin, polyvinylpyrrolidone, sugar syrup, starch and paste may be used as binders.

Talcum, starch and solid polyethylene glycols can serve as lubricants.

The anti-glutinants which can be used include calcium and magnesium stearates, stearic acid and liquid paraffins.

Hard greases and triglycerides are suitable as a support composition for suppositories.

Example for a tablet with 15 mg of active compound:

```
15 mg of active compound I
65 mg of lactose
60 mg of maize starch
 5 mg of polyvinyl pyrrolidone
 4 mg of talcum
 1 mg of magnesium stearate
150 mg Example for a suppository:
  50 mg         of active principle I
1950 mg         of hard grease
  2g.
```

The compound I according to the invention can be used in medicines for the treatment of rheumatic diseases. For oral use, doses of 15 and 30 mg, administered twice to three times per day are for example useful.

Doses for 50 mg can be used for suppositories. For local administration, semi-solid and liquid preparations with 2 to 5% of active principle are suitable.

EXAMPLE 1 a.

[1-(p-Chlorobenzoyl)-5-methoxy-2-methyl-3-indoleacetoxy]-benzyl acetate 5 g (0.016 mol) of $N^{(1)}$-(p-methoxyphenyl)-p-chlorobenzhydrazide hydrochloride and 4.75 g (0.018 mol) of benzyl levulinoyloxyacetate were heated in 25ml of glacial acetic acid for 3 hours at 80°C. The solvent was then evaporated off under vacuum, the residue was taken up in chloroform and the solution was washed neutral by shaking with sodium bicarbonate solution and thereafter with water. After drying the chloroform solution, this was subjected to chromatography on aluminium oxide, the eluate was concentrated by evaporation and the viscous oil remaining as residue was crystallised by adding ether. The compound melted at 94°–95°C. The yield was 4.1 g which corresponds to 50.7% of the theoretical yield.

b.

[1-(p-Chlorobenzoyl)-5-methoxy-2-methyl-3-indoleacetoxy]-acetic acid 25.4 g (0.050 mol) of [1-(p-chlorobenzoyl)-5-methoxy-2-methyl-3-indoleacetoxy]-benzyl acetate were dissolved in 400 ml of glacial acetic acid and hydrogenated on 2.0 g of palladium carbon at room temperature. After the absorption of hydrogen had finished (1 hour), the catalyst was filtered off, the filtrate was concentrated by evaporation under vacuum and the compound was caused to crystallise by adding petroleum ether. The compound melted at 149.5°–150.5°C (determined on the micro-Kofler bench); the yield was 19.4 g which corresponds to 93% of the theoretical yield.

For $C_{21}H_{18}ClNO_6$: Calculated: C, 60.72% H, 4.36% Cl, 8.52% N, 3.36%. Found: C, 61.36% H, 4,39% Cl, 8.45% N, 3.39%.

The sodium salt was obtained by titration of a solution of the acid in methanol with a solution of sodium in methanol.

EXAMPLE 2 a.

[1-(p-Chlorobenzoyl)-5-methoxy-2-methyl-3-indoleacetoxy]-benzylacetate 5.2 g of p-methoxyphenylhydrazine were suspended in 25 ml of glacial acetic acid and 90 ml of water and 10 g of benzyl levulinoyloxyacetate were slowly added at room temperature while stirring. After stirring for 1 hour, the mixture was extracted by shaking with toluene, the toluene solution was washed neutral with water, dried and concentrated. 15.1 g of benzyl levulinoyloxyacetate (p-methoxyphenyl)-hydrazone were obtained as a brownish oil, which was not purified but was dissolved in 25 ml of absolute pyridine, and then 100 ml of ether were added and mixed with a solution of 8.7 g of p-chlorobenzoyl chloride in 50 ml of ether at 0°C with the introduction of nitrogen. After boiling for 2 hours under nitrogen, the solution was cooled, washed neutral with water, dried and concentrated by evaporation. 19 g (crude yield) of $N^{(2)}$-(p-chlorobenzoyl)-$N^{(2)}$-(p-methoxyphenyl)-hydrazone of benzyl levulinoyloxyacetate were obtained. This product was further treated without purification, by taking it up in 75 ml of glacial acetic acid and heating for 5 hours at 80°C. After evaporating off the glacial acetic acid under vacuum, the further treatment was carried out as described in Example 1. The yield of [1-(p-chlorobenzoyl)-5-methoxy-2-methyl-3-indoleacetoxy]-benzyl acetate amounted to 11% of the theoretical, based on the total amount of hydrazine.

b.

[1-(p-Chlorobenzoyl)-5-methoxy-2-methyl-3-indoleacetoxy]-acetic acid 50.6 g (0.1 mol) of [1-(p-chlorobenzoyl)-5-methoxy-2-methyl-3-indoleacetoxy]-benzyl acetate were hydrogenated in 300 ml of absolute dimethylformamide in the presence of 5 g of 5% palladium carbon at 20°C within 15 minutes, with absorption of the calculated quantity of hydrogen. About 200 ml of water were added to the hydrogenation product, filtered through kieselguhr, until clouding started to occur and the solution was allowed to crystallise at 5°C. The crystallisate was suction-filtered, washed with water and dried under vacuum. The yield of [1-(p-chlorobenzoyl)-5-methoxy-2-methyl-3-indoleacetoxy]-acetic acid amounted to 39 g which corresponds to 94% of the theoretical yield. The compound melted at 148°–149°C as determined on the Mettler melting point apparatus.

EXAMPLE 3

180 g (0.503 mol) of 1-(p-chlorobenzoyl)-5-methoxy-2-methyl-3-indoleacetic acid were dissolved in 900 ml of dimethylformamide, 35 g of triturated, anhydrous potassium carbonate were added and stirring was continued for 45 minutes at 50°C. 128 g (0.558 mol) of benzyl bromoacetate were then added and the mixture was stirred for 3 hours at 50°C. After evaporating the dimethylformamide under vacuum, the residue was dissolved in chloroform, washed several times with water, dried over sodium sulphate and then separated by chromatography on alumina. The eluate was concentrated by evaporation and the residue re-crystallised from alcohol. The [1-(p-chlorobenzoyl)-5-methoxy-2-methyl-3-indoleacetoxy]-benzyl acetate which formed melted at 93°–94°C and the yield was 81% of the theoretical. This benzyl ester was converted as described in Example 1 or 2 into the free acid.

EXAMPLE 4

1.83 g (0.005 mol) of (5-methoxy-2-methyl-3-indoleacetoxy)-benzyl acetate were mixed with 5 g ( 0.022 mol) of the mixed anhydride between monoethylcarbonate and p-chlorobenzoic acid and 0.1 ml of triethylamine and slowly heated at 120°–130°C (bath temperature). After the evolution of carbon dioxide had ended (30 minutes), the mixture was cooled, dissolved in ethyl acetate, then washed with a common salt solution and the organic phase was dried over sodium sulphate. The solution was filtered, concentrated and the compound caused to crystallise by adding ether. The yield of [1-(p-chlorobenzoyl)-5-methoxy-2-methyl-3-indoleacetoxy]-benzyl acetate amounted to 0.7 g which corresponds to 28% of the theoretical yield and the compound melted at 93°–94°C. It was converted in the manner indicated into the free acid.

EXAMPLE 5

1.84 g of (5-methoxy-2-methyl-3-indoleacetoxy)-benzyl acetate in 19 ml of dimethylformamide, was added to 0.51 g of a suspension of sodium hydride in 20 ml of dimethylformamide, stirred for 20 minutes at 0°C under nitrogen and then 1.19 mol of p-chlorobenzoyl chloride were introduced. The mixture was stirred for 5 hours under nitrogen at 0° to 5°C and thereafter introduced into 115 ml of ether, 115 ml of glacial acetic acid and 230 ml of iced water. The layers were separated and the aqueous phase was extracted by shaking several times with ether. The combined ethereal phases were washed with water, dried and concentrated by evaporation under vacuum. 1.7 g of a crude product were obtained and this was purified by chromatography from cyclohexane-glacial acetic acid (3:1) on kieselguhr. The yield was 0.3 g which corresponds to 11.9% of the theoretical yield with a melting point of 92-94°C. The [1-(p-chlorobenzoyl)-5-methoxy-2-methyl-3-indoleacetoxy]-benzyl acetate which formed was converted in the manner indicated into the free acid.

The (5-methoxy-2-methyl-3-indoleacetoxy)-benzyl acetate was prepared in the manner described below:

225 g of 92% 4-methoxyphenylhydrazine hydrochloride and 374 g of levulinoyl benzyloxyacetate were suspended in 1.3 liters of glacial acetic acid and stirred for 1 day at room temperature. Thereafter, the temperature was slowly raised to 50°C and the mixture was stirred for another 3 hours. The glacial acetic acid was then substantially distilled off under vacuum and the residue introduced into iced water. The aqueous phase was extracted several times with toluene, the combined toluene extracts were washed with a sodium carbonate solution and then with water, dried, concentrated by evaporation and the residue was subjected under vacuum to a molecular distillation. 328 g which corresponds to 74% of the theoretical yield of (5-methoxy-2-methyl-3-indoleacetoxy)-benzyl acetate were obtained with a boiling point of 210°C at 0.001 mm Hg.

Reaction schemes

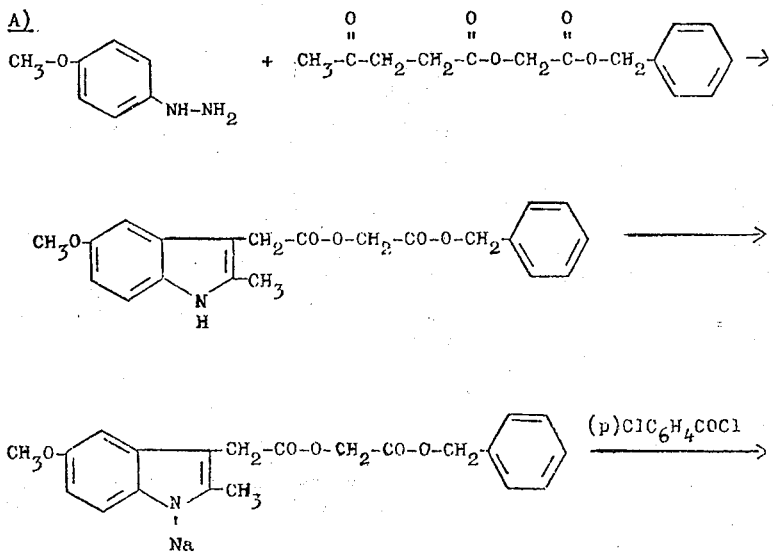

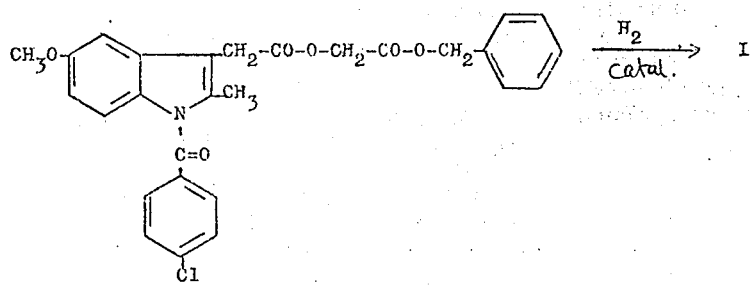
B)
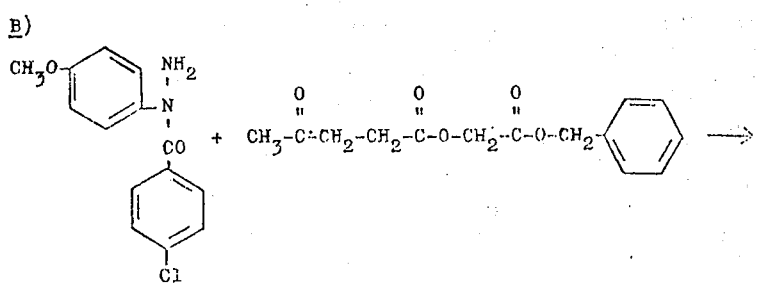
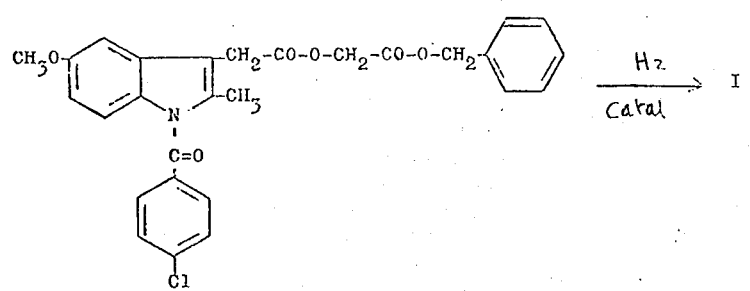
C)
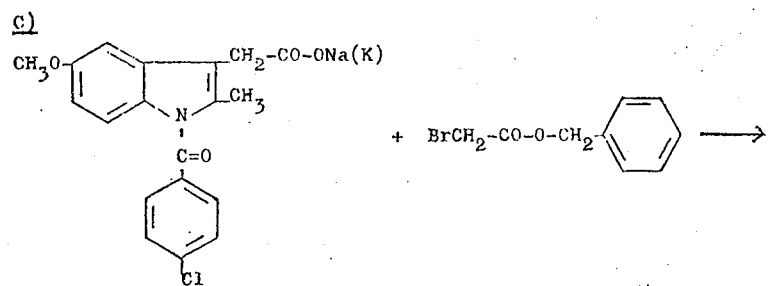
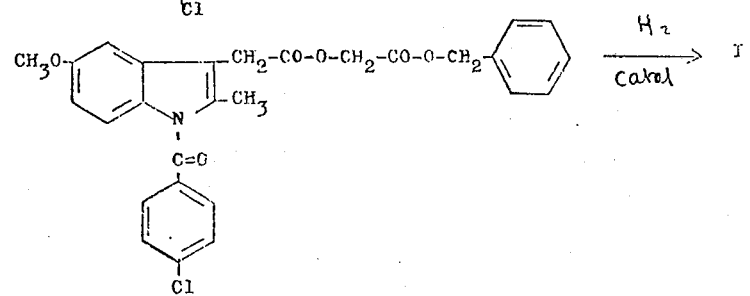
D)
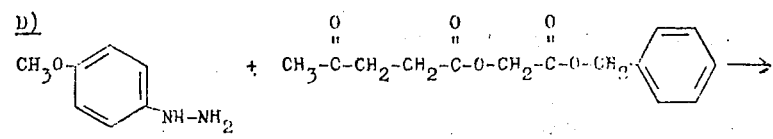

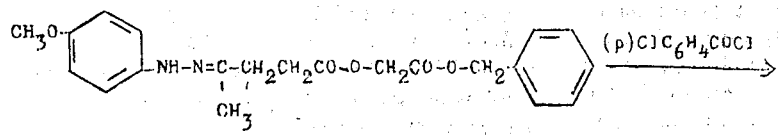
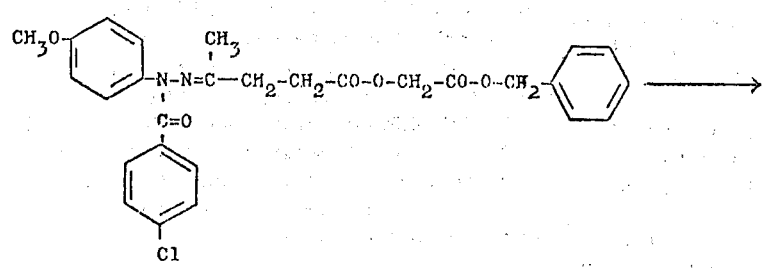
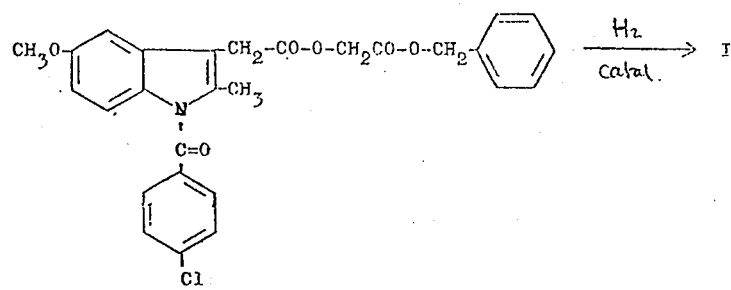
E)
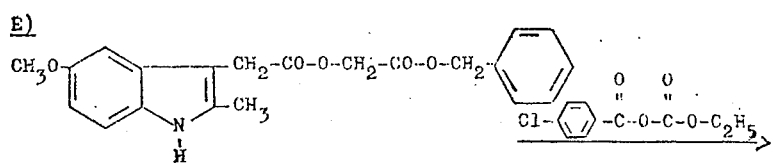
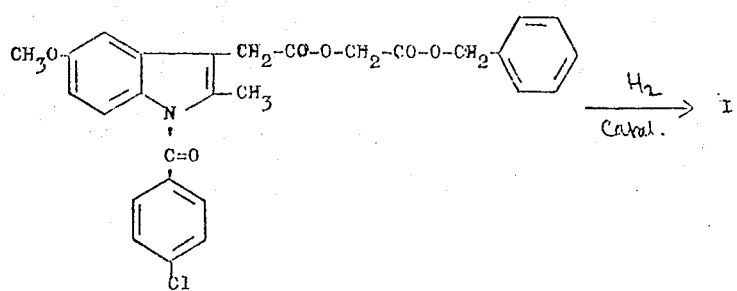

What we claim is:

1. A pharmacological preparation for treating inflammation which comprises an anti-phlogistically effective amount of [1-(p-chlorobenzoyl)-5-methoxy-2-methyl-3-indole]-acetoxyacetic acid, or a salt thereof with a pharmacologically acceptable base, in admixture with a pharmaceutically acceptable carrier.

2. A preparation as claimed in claim 1 in which the pharmaceutically acceptable carrier comprises at least one of a filler, disintegrating agent binder, lubricant and an anti-agglutinant.

3. A pharmacological preparation as claimed in claim 1 comprising as the active ingredient [1-(p-chlorobenzoyl)-5-methoxy-2-methyl-3-indole]-acetoxyacetic acid.

4. A pharmacological preparation as claimed in claim 1 comprising as the active ingredient an [1-(p-chlorobenzoyl)-5-methoxy-2-methyl-3-indole]-acetoxyacetic acid salt of an inorganic base.

5. A pharamacological preparation as claimed in claim 1 comprising as the active ingredient an [1-(p-chlorobenzoyl)-5-methoxy-2-methyl-3-indole]-acetoxyacetic acid salt of an organic base.

6. A pharamacological preparation as claimed in claim 1 comprising as the active ingredient [1-(p-chlorobenzoyl)-5-methoxy-2-methyl-3-indole]-acetoxyacetic acid sodium salt.

7. Method of treating inflammation which comprises administering to a subject in need thereof a therapeutically effective amount of [1-(p-chlorobenzoyl)-5-methoxy-2-methyl-3-indole]-acetoxyacetic acid or a pharmacologically acceptable salt thereof.

8. Method as claimed in claim 7 wherein said [1-(p-chlorobenzoyl)-5-methoxy-2-methyl-3-indole]-acetoxyacetic acid is in the form of its sodium salt.

9. Method as claimed in claim 8 wherein said [1-(p-chlorobenzoyl)-5-methoxy-2-methyl-3-indole]-acetoxyacetic acid or a pharmacologically acceptable salt thereof is administered at a dosage of about 1.5 mg/kg of body weight of the subject.

* * * * *

UNITED STATES PATENT AND TRADEMARK OFFICE
CERTIFICATE OF CORRECTION

PATENT NO. : 3,966,956
DATED : June 29, 1976
INVENTOR(S) : Karl-Heinz Boltze, et al It is certified that error appears in the above—identified patent and that said Letters Patent are hereby corrected as shown below:

Column 6, line 43
"= -O-C-COCH"     should read   = -O-C-COOH

Column 8, line 18
"4,39%"     should read   4.39%

Column 16, line 16
"8"     should read   7

Signed and Sealed this

Twenty-sixth Day of October 1976

[SEAL]

Attest:

RUTH C. MASON
*Attesting Officer*

C. MARSHALL DANN
*Commissioner of Patents and Trademarks*